United States Patent
Dillen (10) Patent No.: US 10,595,796 B2
(45) Date of Patent: Mar. 24, 2020

(54) MIXED-MODE X-RAY DETECTOR

(71) Applicant: TELEDYNE DALSA B.V., Eindhoven (NL)

(72) Inventor: Bartholomeus Goverdina Maria Henricus Dillen, Geldrop (NL)

(73) Assignee: TELEDYNE DALSA B.V., Eindhoven (NL)

(*) Notice: Subject to any disclaimer, the term of this patent is extended or adjusted under 35 U.S.C. 154(b) by 0 days.

(21) Appl. No.: 16/314,799

(22) PCT Filed: Jul. 5, 2016

(86) PCT No.: PCT/EP2016/065782
§ 371 (c)(1),
(2) Date: Jan. 2, 2019

(87) PCT Pub. No.: WO2018/006937
PCT Pub. Date: Jan. 11, 2018

(65) Prior Publication Data
US 2019/0307407 A1 Oct. 10, 2019

(51) Int. Cl.
*A61B 6/00* (2006.01)
*A61B 6/14* (2006.01)
(Continued)

(52) U.S. Cl.
CPC ............ *A61B 6/14* (2013.01); *A61B 6/03* (2013.01); *A61B 6/032* (2013.01); *A61B 6/4085* (2013.01);
(Continued)

(58) Field of Classification Search
None
See application file for complete search history.

(56) References Cited

U.S. PATENT DOCUMENTS

| 6,049,584 A | 4/2000 | Pfeiffer |
| 2009/0160947 A1 | 6/2009 | Shigeta et al. |

(Continued)

FOREIGN PATENT DOCUMENTS

| EP | 1202561 A2 | 5/2002 |
| EP | 2221003 A1 | 8/2010 |
| EP | 2624539 A2 | 8/2013 |

OTHER PUBLICATIONS

International Search Report for International Application No. PCT/EP2016/065782 dated Nov. 2, 2016.
(Continued)

*Primary Examiner* — Hoon K Song
(74) *Attorney, Agent, or Firm* — K&L Gates LLP (57) ABSTRACT

The present invention is related to an X-ray detector and to an X-ray detector system comprising the X-ray detector. It is further related to an X-ray system and to a method for obtaining an X-ray image.

According to the invention, the X-ray detector is configured to be operable in a mixed read-out mode in which an output of the X-ray sensor comprises sequentially obtained first blocks, each first block comprising a plurality of sequentially obtained different second blocks, wherein each second block comprises a read-out of the target segment, and wherein more than one of the second blocks comprises a different part of the additional segments such that each first block comprises a read-out for each of the plurality of segments.

22 Claims, 4 Drawing Sheets

(51) Int. Cl.
　　　*A61B 6/03*　　　(2006.01)
　　　*H04N 5/32*　　　(2006.01)
　　　*H04N 5/345*　　(2011.01)
　　　*G01T 1/00*　　　(2006.01)
　　　*A61B 6/06*　　　(2006.01)
　　　*H04N 5/355*　　(2011.01)

(52) U.S. Cl.
　　　CPC .......... *A61B 6/4208* (2013.01); *A61B 6/4441* (2013.01); *G01T 1/00* (2013.01); *H04N 5/32* (2013.01); *H04N 5/345* (2013.01); *H04N 5/3456* (2013.01); *A61B 6/06* (2013.01); *H04N 5/3559* (2013.01)

(56) References Cited

U.S. PATENT DOCUMENTS

| | | | |
|---|---|---|---|
| 2009/0168966 A1* | 7/2009 | Suzuki | A61B 6/032 378/116 |
| 2013/0308846 A1 | 11/2013 | Chen et al. | |
| 2015/0103973 A1 | 4/2015 | Liu et al. | |

OTHER PUBLICATIONS

Written Opinion of the International Searching Authority for International Application No. PCT/EP2016/065782 dated Nov. 2, 2016.
International Preliminary Report on Patentability for International Application No. PCT/EP2016/065782 dated Sep. 20, 2018.

* cited by examiner

MIXED-MODE X-RAY DETECTOR

PRIORITY

This application is a U.S. National Stage Entry under 35 U.S.C. § 371 of International Application No. PCT/EP2016/065782, entitled MIXED-MODE X-RAY DETECTOR, filed Jul. 5, 2016, the contents of which is incorporated herein by reference in its entirety and for all purposes.

The present invention is related to an X-ray detector and to an X-ray detector system comprising the X-ray detector. It is further related to an X-ray system and to a method for obtaining an X-ray image.

X-ray systems are widely employed in the field of Non-Destructive Testing (NDT) and dentistry, such as oral surgery, endodontics and orthodontics. X-ray medical imaging can for instance be used in treatment planning and diagnosis.

An X-ray system typically comprises an X-ray source provided with an emitter for emitting X-rays and a collimator for collimating the emitted X-rays, wherein the collimator comprises collimator blades. These systems further comprise an X-ray detector. Such detector comprises an X-ray sensor that comprises a plurality of segments, addressing circuitry for individually addressing the segments, and read-out circuitry for reading out an addressed segment.

To obtain information from multiple view angles, the system can be provided with a mounting frame for moving the X-ray source and X-ray detector around an object to be imaged. This allows the irradiation of X-rays from different angles towards the object. The mounting frame may for instance comprise a rotatable C-arm, wherein the X-ray source and X-ray detector are mounted on opposing ends of the C-arm in a fixed relationship to each other. The C-arm is able to rotate relative to the object to be imaged.

An X-ray system as described above can be used to obtain panoramic X-ray images. These images are constructed using X-ray images obtained from different view angles, wherein the different X-ray images are processed to form a single panoramic image. Panoramic (PAN) images allow a dentist to gain an overall impression of a person's dental condition. When obtaining a panoramic X-ray image only a part of the available X-ray sensor is used. More in particular, only information acquired using a target segment among the plurality of segments is used. The other segments, referred to as additional segments, are not read out. Generally, when obtaining a panoramic image, the collimator blades are in a first, partially opened position.

Another mode that can be supported by most of the known X-ray systems is Cone Beam Computed Tomography (CBCT). In this mode, the X-ray detector and X-ray source are also rotated around the object to be imaged. However, in this mode all segments of the X-ray sensor are read out. This information is used to construct a 3D model of the object to be imaged. Hence, compared to the Panoramic mode, the process is relatively slow and the X-ray dose that the patient is subjected to is generally larger. Generally, when obtaining a CBCT 3D model, the collimator blades are in a second position, in which position more X-rays may pass compared to the first position.

Generally, the CBCT mode provides superior image information compared to panoramic images. For example, the object can be analysed in three dimensions. Due to the differences in time required for making a scan and the differences in effective dose rates, and doses, Panoramic images are mostly used for relatively straightforward analysis, whereas CBCT images are used when more in-depth information is needed, for example when geometrically correct information is to be obtained in view of an implant to be placed.

The applicant has found that it is currently not possible to achieve the high frame rates and fast imaging processes typically encountered with Panoramic scans when operating in the CBCT mode.

Further to the above, a dentist generally uses either the Panoramic image or the CBCT based 3D model to perform a diagnosis or to set up a treatment plan. Each of these techniques presents its own advantages or short comings. In some cases, this approach may be inaccurate or insufficient. It is an object of the present invention to alleviate this problem without significantly increasing the X-ray dosage that a patient is subjected to.

According to the invention, this object has been achieved using the X-ray detector of claim 1 which is characterized in that the X-ray detector is configured to be operable in a mixed read-out mode in which an output of the X-ray sensor comprises sequentially obtained first blocks, each first block comprising a plurality of sequentially obtained different second blocks. According to the invention, the following conditions are met:

- each second block comprises a read-out of the target segment
- more than one of the second blocks comprises a different part of the additional segments
- each first block comprises a read-out for each of the plurality of segments In the following examples, the X-ray sensor comprises one target segment T and eight additional segments A1-A8. Furthermore, "||" denotes a boundary between first blocks, "|" a boundary between second blocks, and T;A1 indicates that segment T and A1 are read out.

Using the notation above, the following sequences are examples of the mixed read-out mode according to the invention:

1. ||T;A1|T;A2|T;A3|T;A4|T;T|T;A5|T;A6|T;A7|T;A8||

In this sequence, each second block comprises a read-out of two different segments of which one of the target segment. One second block comprises two read-outs of the target segment. However, such second block may be omitted as sufficient information about segment T may already have been obtained from the temporally adjacent second blocks |T;A4| and |T;A5|:

2. ||T;A1|T;A2|T;A3|T;A4|T;A5|T;A6|T;A7|T;A8||

Alternatively, this second block may comprise only one read-out of the target segment:

3. ||T;A1|T;A2|T;A3|T;A4|T|T;A5|T;A6|T;A7|T;A8||

According to the invention, not every second block may comprise a read-out of an additional segment:

4. ||T;A1;A2|T||T;A3|T;A4|T|T;A5|T;A6|T;A7|T;A8||

In this case, the $2^{nd}$ second block above may also be omitted. Hence, the invention does not exclude embodiments wherein the second blocks have different sizes.

Typically, Panoramic scans are obtained at relatively high frame rates to avoid blurring of the image due to the rotational movement of the detector around the object to be imaged. As such, the addressing circuitry and read-out circuitry are operating at relatively high speeds.

The general concept of the present invention is to use the addressing and read-out speed headroom that is offered by contemporary sensors to perform a read-out of the target segment and a part of the additional segments without reducing the sharpness of the final image(s). This allows a Panoramic image to be obtained as well as a CBCT based 3D model. Consequently, the dentist is able to use two different sources of information. Compared to a regular CBCT scan, the total dosage a patient is subjected to is not significantly increased.

The addressing circuitry may be configured to, for said more than one of the second blocks, sequentially address the target segment and said different part of the additional segments, when the X-ray detector operates in the mixed read-out mode. As an example, in the first example above, the addressing circuitry may address, in the order presented here, T and A1. In a next second block, the addressing circuitry may address, in the order presented here, T and A2.

The number of second blocks may equal the number of additional segments. Additionally or alternatively, each of the second blocks may comprise a read-out for a different part of the additional segments. In an embodiment, each second block comprises a read-out of the target segment and a single additional segment.

The X-ray detector may further be operable in a first regular read-out mode, in which an output of the X-sensor comprises sequentially obtained third blocks, each third block comprising a single read-out for each of the plurality of segments. The first regular read-out mode corresponds to the known CBCT scan mode.

Additionally or alternatively, the X-ray detector may further be operable in a second regular read-out mode, in which an output of the X-sensor comprises sequentially obtained fourth blocks, each fourth block only comprising a single read-out for the target segment. The second regular read-out mode corresponds to the known Panoramic scan mode.

The segments of the X-ray sensor may be adjacently arranged in a given direction.

An X-ray detector may comprise an X-ray sensor having a plurality of pixels, which pixels are arranged in rows and columns. Each of the plurality of segments may correspond to a group of rows, preferably to a group of adjacent rows. As an example, each of the plurality of segments corresponds to an identical number of adjacent rows.

The X-ray sensor may comprise a CMOS based X-ray sensor, wherein each pixel comprises a photosensitive element and a storage capacitor, wherein the photosensitive element is configured to change a voltage over the storage capacitor in dependence of an amount of incident photons. For example, each pixel may comprise a PIN diode that is coupled to a storage capacitor. The pixel may further comprise a scintillator layer that converts incoming X-rays into visible light. This latter light is detected by the PIN diode, which generates a current into or out of the storage capacitor. As a result, the voltage over the storage capacitor changes when X-rays fall onto the pixel. In other embodiments, the photosensitive element is configured to directly detect incoming X-ray photons, i.e. without prior conversion to visible light.

The pixels of the X-ray sensor may be multi-well pixels that are capable of operating in at least a high full-well mode and in a low full-well mode, wherein a storage capacitance of the pixel in the high full-well mode is substantially larger than that in the low full-well mode. Moreover, the X-ray detector may further comprise a well selector for selecting the low or high full-well mode for all pixels in a given segment. Hence, although the invention does not exclude selecting a full-well mode for each pixel individually, it is preferred if such selection is made for all the pixels that belong to a given segment.

For example, the well selector may be configured to select the high full-well mode for the pixels in the additional segments and to select the low full-well mode for the pixels in the target segment, when the X-ray detector is operating in the mixed read-out mode.

Typically, a pixel can be reset before the start of each read-out cycle. During the reset, the voltage over the storage capacitor is set to a predefined voltage. After resetting the pixel, the voltage over the storage capacitor will change due to the current generated by the PIN diode as a result of incoming X-rays. When the pixel is addressed, the voltage at that time is read-out. The difference between that voltage and the predefined voltage is a measure for the amount of X-rays that fell onto the pixel during the period between reset and read-out. This period is normally referred to as the integration time.

Using a long integration time in combination with a suitable storage capacitance provides acceptable signal-to-noise ratios. If the integration time is too small, the change in voltage over the storage capacitor will only be marginal, whereas if the integration time is too large, the voltage will saturate.

In the mixed read-out mode, the resetting of the pixels may be done in such a manner that the time between consecutive resets is substantially equal to the time between consecutive read-outs. For example, each pixel may be reset after it has been read out. In this way, the pixel will continue to obtain X-ray information until the next read-out.

When resetting the pixels as described above, it becomes apparent that pixels belonging to the target segment are read out more often in the mixed read-out mode than the additional segments. For instance, if each second block comprises a single read-out for the target segment and a single read-out for one of 10 additional segments, the integration time for pixels in the target segment will roughly be a factor 10 smaller than the integration time for pixels in the additional segments. In these cases it may therefore be advantageous to use a high full-well mode for the pixels in the additional segments whereas pixels in the target segment can be put in the low full-well mode.

If all the pixels have the same full-well storage capacitance, a risk exists in that the pixels in the additional segments may saturate or that the pixels in the target segment do not provide an acceptable signal-to-noise ratio.

The well selector may be configured to select the same full-well mode for the pixels in the additional segments and the target segment when the X-ray detector is operating in the first regular read-out mode. In the first regular mode, corresponding to a CBCT scan mode, each segment is read out with roughly the same integration time for the pixels. As such, there is less need to differentiate between the pixels in the target segment and the additional segments.

The well selector may also be configured to select the same full-well mode for the pixels in the additional segments and the target segment when the X-ray detector is operating in the second regular read-out mode. During this read-out mode, information from the additional segments is normally discarded. More in particular, collimator blading is typically used to limit X-ray irradiation to the target segment causing little to no X-rays to fall onto the additional segments. Nevertheless, the present invention does not exclude using a lower full-well mode for the pixels in the additional segments in this case to capture any information that may still fall onto the pixels in the additional segments.

The present invention also provides an X-ray detector system that comprises the X-ray detector as described above. The X-ray detector system further comprises an image constructor configured for constructing a first X-ray image based on the read-outs of the target segment and a second X-ray image or 3D model based on the read-outs of the additional segments and a read-out of the target segment, when the X-ray detector is operating in the mixed read-out mode. The image constructor may be configured to adjust the first X-ray image using the second X-ray image or 3D model.

For constructing the first X-ray image and the second X-ray image or 3D model an identical read-out for the target segment may be used. Typically, the read-out of the target segment that is used for this purpose is the read-out that would follow or precede the read-out of an additional segment that is adjacent to the target segment. For instance, if the target segment is located in the middle between 8 additional segments, the read-out of the target segment that follows or precedes the read-out of the fourth or fifth additional segment would be used for constructing the second X-ray image or 3D model.

The image constructor may comprise a first image unit for constructing the first X-ray image, a second image unit for constructing the second X-ray image or 3D model, a buffer unit for receiving a second block from the read-out circuitry of the X-ray detector, and a relay unit for relaying read-outs pertaining to the target segment in the received second block to the first image unit and for relaying read-outs pertaining to an additional segment in the received second block to the second image unit.

The image constructor may be configured to adjust the first X-ray image using the second X-ray image or 3D model.

The first X-ray image may correspond to a panoramic image. Additionally or alternatively, the 3D model may comprise a digital volume of the object, wherein the image constructor is preferably configured to generate the 3D model using Cone Beam Computed Tomography (CBCT).

The present invention further provides an X-ray system that comprises an X-ray source provided with an emitter for emitting X-rays and a collimator for collimating the emitted X-rays. The system further comprises the X-ray detector system as described above, a mounting frame for moving the X-ray source and X-ray detector around the object to irradiate X-rays from different angles towards the object. The X-ray system is configured to obtain a plurality of read-outs of the plurality of segments corresponding to different angles of incidence of the X-rays relative to the object.

The system may comprise a controller configured for controlling the X-ray source and the X-ray detector, wherein the controller is further configured for providing a control signal to the addressing circuitry to set the X-ray detector in a read-out mode among the mixed read-out mode, the first regular read-out mode, and the second regular read-out mode. The controller may further be configured for providing a full well select signal to the X-ray sensor to set the full well capacitance in the pixels of the X-ray sensor.

The mounting frame may be configured to move between angular positions with respect to the object, while the X-rays are being irradiated and while the read-outs of the plurality of segments are obtained. Alternatively, the mounting frame may be configured to move between discrete angular positions with respect to the object, at which positions the X-rays are irradiated and the read-outs of the plurality of segments are obtained.

The collimator blades may be configured to limit X-ray irradiation to the target segment when the X-ray detector operates in the second regular read-out mode. The collimator blades may also be configured to limit X-ray irradiation to the target segment when the X-ray detector operates in the mixed mode read-out mode. In this case, X-ray scattering processes that occur inside the object the imaged, more in particular inside the region corresponding to the target segment, can be characterized. For instance, X-rays may scatter at metal surfaces inside the object to be imaged. Such X-rays can be captured by the additional segments.

The present invention also provides a method for constructing an X-ray image, which comprises the steps of irradiating X-rays onto an object to be imaged, and collecting X-rays from the object to be imaged using an X-ray sensor, wherein the X-ray sensor comprises a plurality of segments, said plurality of segments comprising a target segment and a plurality of additional segments.

The method according to the invention is characterized by the steps of sequentially obtaining first blocks from the X-ray sensor, each first block comprising a plurality of sequentially obtained different second blocks, wherein each second block comprises a read-out of the target segment, and wherein more than one of the second blocks comprises a different part of the additional segments such that each first block comprises a read-out for each of the plurality of segments, and by the further steps of constructing a first X-ray image based on the read-outs of the target segment, and constructing a second X-ray image or 3D based on the read-outs of the additional segments.

It should be apparent to the skilled person that method steps described in conjunction with the X-ray detector, X-ray detector system, and/or X-ray system can equally be applied in the method according to the invention.

Next, the invention will be described in more detail referring to the appended drawings, wherein.

Figure 1:
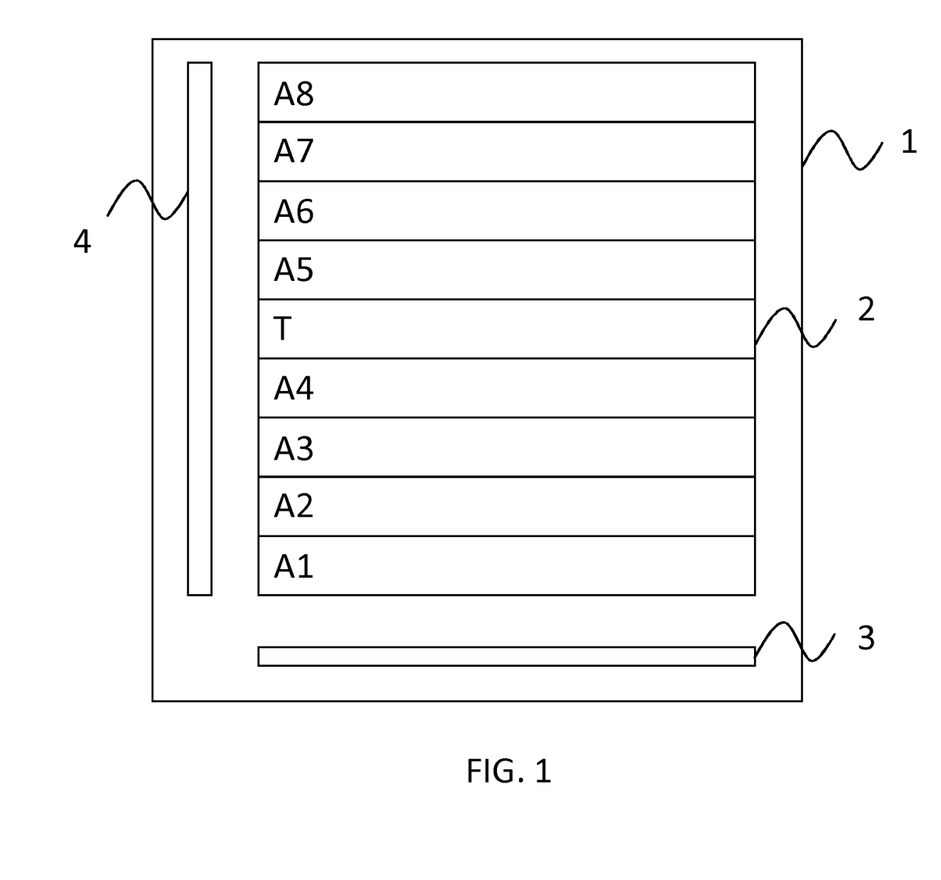
FIG. 1 illustrates a known layout of an X-ray sensor.

FIG. 1 illustrates a known layout of an X-ray detector 1. This sensor comprises an X-ray sensor 2, which in an example comprises one or more CMOS based sensor tiles. Each tile comprises an array of pixels that is arranged in rows and pixels. By combining several tiles a large sensor surface can be obtained.

X-ray sensor 2 is divided into a plurality of segments, comprising a target segment T and a plurality of additional segments A1-A8. Each segment comprises a plurality of pixel rows. It should be appreciated by the skilled person that the division into 9 segments is for illustrative purposes only and that other segmentations are possible without deviating from the invention.

For instance, assuming an X-ray sensor 2 comprising 900 pixel rows, each row comprising 900 pixels, segments can be formed using 100 pixel rows each. Hence, in this example each segment would comprise 100×900 pixels.

It should be noted that the segmentation above is generally a purely mathematical division of X-ray sensor 2. It generally does not correspond to a physical segmentation.

Each of the pixel rows is sequentially addressed by addressing circuitry 4. This circuitry may comprise a 1-bit shift register of which the starting position can be set. When the bit shifts through the register, different pixel rows are addressed.

The X-ray detector further comprises read-out circuitry 3 for reading out an addressed pixel row. In general, only a single pixel row can be addressed and read out at the same time.

Figure 2:
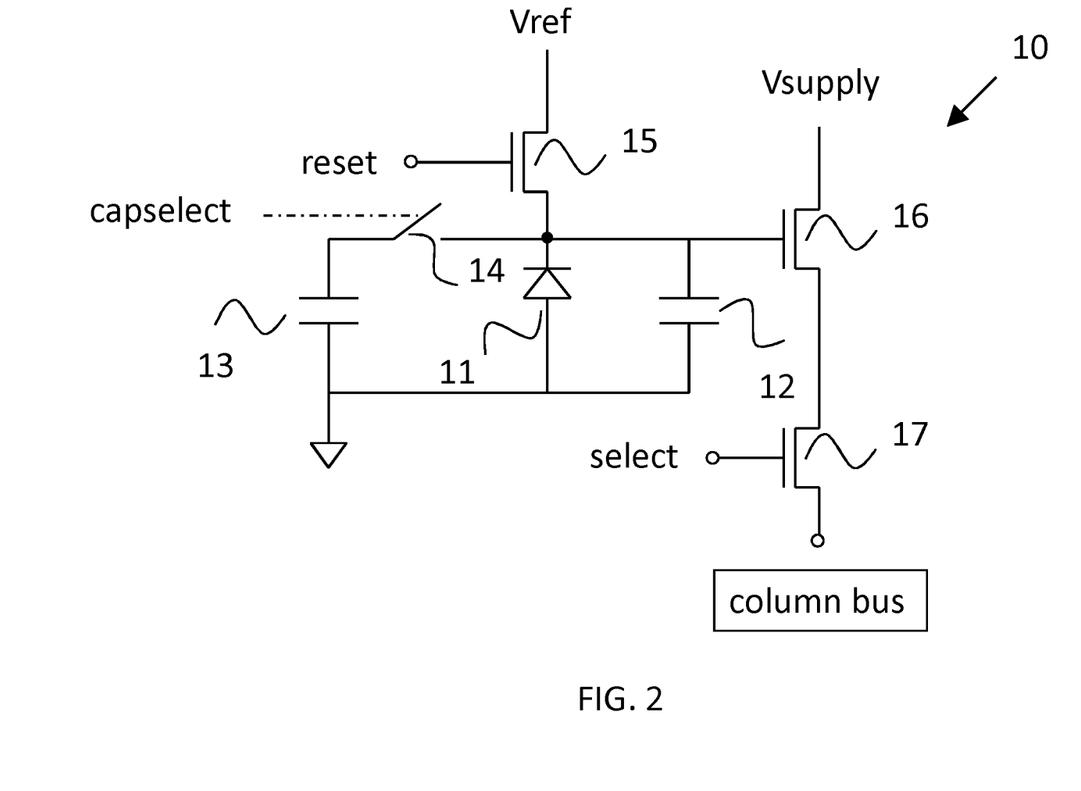
FIG. 2 illustrates a known pixel schematic used in the X-ray sensor.

FIG. 2 presents an example of a known schematic for a pixel 10, referred to as a 3T schematic. The pixel comprises a (pinned) photodiode 11, a primary storage capacitor 12, and a secondary storage capacitor 13 which can be switched using a switch 14. Typically, a scintillator layer (not illustrated) is applied over the pixel or is integrated therewith. This layer converts incoming X-rays into visible light which can be detected by photodiode 11.

The operation of the pixel can be explained as follows. As a first step, the voltage at the terminal between capacitor 12 and photodiode 11 is charged/reset to a predefined reference voltage Vref using a NMOST 15 in response to a reset signal received from the a row driver comprised in addressing circuitry 4. Next, NMOST 15 is brought into in a non-conducting state. When light falls onto photodiode 11, it generates charges which are transferred to capacitor 12. Consequently, the voltage at the terminal of capacitor 12 will decrease depending on the incident light. After a predetermined time, e.g. the integration time, the voltage at this terminal is sensed using a source follower NMOST 16 that is connected to an NMOST 17 that acts as a selection FET. More in particular, in response to a select signal from the row driver, the voltage at the terminal of capacitor 12 is fed through source follower 16 and selection FET 17 to the read-out circuitry via a pixel column bus. There, the analog signal is converted into a digital value using an analog-to-digital converter. As a final step, selection FET 17 is brought into a non-conductive state and the process is repeated.

By closing switch 14, in response to receiving a capacitance select signal from the row driver, secondary storage capacitor 13 can be put parallel to primary storage capacitor 12. This allows the pixel to process a higher dose of X-rays as the effective storage capacitance has increased, and to thereby offer a different sensitivity.

In general, the select and reset control signals mentioned above are provided by addressing circuitry 4. Moreover, this circuitry may comprise the abovementioned shift register as well as the row drivers for providing the various control signals to the pixels in a given pixel row.

According to the invention, the output of the X-ray detector comprises a plurality of first blocks when operating in the mixed read-out mode. In that case, some of the first blocks comprise read-outs for different segments. To that end, the target segment and an additional segment are sequentially addressed.

As an example, assume that first additional segment, e.g. A1, and target segment T are read out. In the example above with X-ray sensor 2 having 900 pixel rows, these segments correspond to pixel rows 1-100 and pixel rows 401-500. When acquiring the read-outs of these segments, the addressing circuitry according to the invention may first address row 1 of segment A1, and then row 2 of segment A1 and so on until row 100 has been reached. After reading out this pixel row, the starting position of the shift register may be changed to pixel row 401 after which the pixel rows of target segment T can be read out. It should be noted that the present invention is not limited to this particular manner of addressing of the pixel rows or segments. For instance, it may equally be possible to first address pixel row 1 of segment A1, then pixel row 401 of segment T, then pixel row 2 of segment A1, and then pixel row 402 of segment T, and so on.

Various sensing schemes are known to the skilled person, for instance to correct for a process-related spread in the threshold voltages of the various MOSTs. The present invention is not limited to the particular pixel schematic shown in FIG. 2, nor to the particular manner of operation described above.

Figure 3:
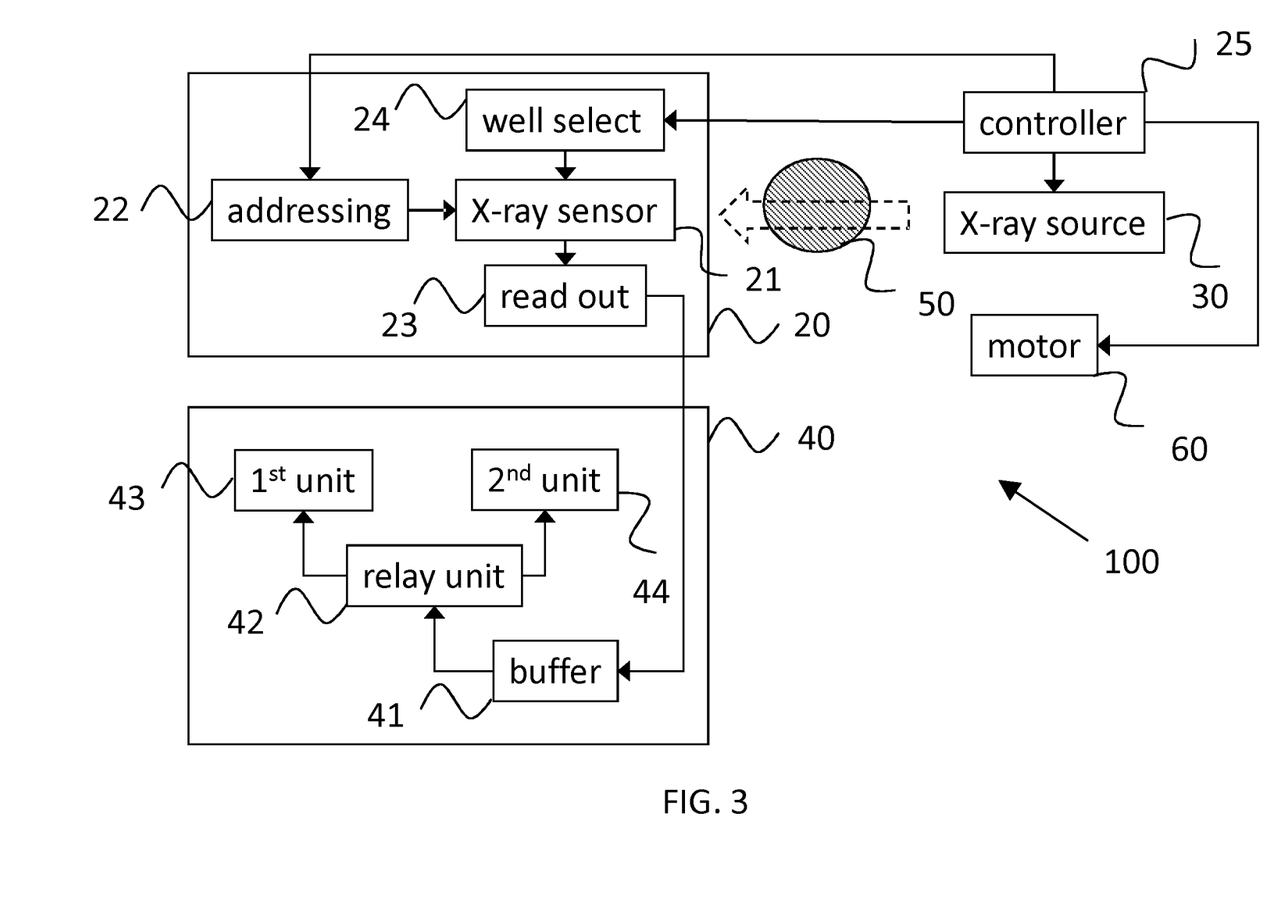
FIG. 3 illustrates an embodiment of an X-ray system in accordance with the invention.

FIG. 3 illustrates an X-ray system 100 according to the invention. System 100 comprises an X-ray detector 20, an X-ray source 30, an image constructor 40, a motor 60, and a controller 25. System 100 is arranged to image an object 50 by means of X-ray irradiation. This can be performed by rotating X-ray source 30 and X-ray sensor 20 around object 50. To this end, controller 25 may control motor 60 that rotates a C-arm to which X-ray source 30 and X-ray detector 20 are fixedly mounted, around object 50.

X-ray detector 20 comprises an X-ray sensor 21 that may be embodied similar to the known X-ray sensor 2 in FIG. 1. It further comprises addressing circuitry 22 for addressing the pixel rows/segments of X-ray sensor 21. This circuitry deviates from addressing circuitry 4 illustrated in FIG. 1 due to the fact that circuitry 22 allows for the mixed read-out mode according to the invention.

X-ray detector 20 further comprises read-out circuitry 23 for reading out selected pixel rows/segments. Circuitry 23 may be embodied as the known read-out circuitry 3 of FIG. 1.

X-ray sensor 21 comprises an array of rows and columns of multi-well pixels, such as pixel 10 illustrated in FIG. 2. To select the full-well capacitance, X-ray detector 20 comprises a well selector 24, which provides a well select control signal to the pixels in X-ray sensor 21. Although well selector 24 can be configured to individually set the full-well capacitance of the pixels, it generally suffices when well selector 24 sets the full-well capacitance for all the pixels in a given pixel row.

The output of X-ray detector 20 generally comprises a data stream. This data stream can be divided into a plurality of blocks. For example, assuming segments of 100 pixel rows, each pixel row comprising 900 pixels, the data stream could comprise a plurality of sections that are each related to a given segment N. For instance:

Segment A1=[data pixel 1 in row 1 of segment A1, data pixel 2 in row 1 of segment A1, . . . , data pixel 900 in row 1 of segment A1, data pixel 1 in row 2 of segment A1, data pixel 2 in row 2 of segment A1, . . . , data pixel 900 in row 2 of segment A1, . . . , data pixel 1 in row 100 of segment A1, data pixel 2 in row 100 of segment A1, . . . , data pixel 900 in row 100 of segment A1]

In a similar manner, the data stream could comprise the following sections when X-ray detector 20 is operating in the mixed read-out mode:

||T;A1|T;A2|T;A3|T;A4|T;A5|T;A6|T;A7|T;A8|| where "T" in the sequence above denotes the section for segment T and "An" denotes the section for segment An. As described earlier, "||" denotes a boundary of a first block and "|" a boundary of a second block. The distinction between first and second blocks is in general only relevant when operating in the mixed read-out mode.

The data outputted by read-out circuitry 23 is fed to a buffer 41 in image constructor 40. This data is then processed by relay unit 42. This unit is configured to, when the X-ray detector 20 operates in the mixed read-out mode, relay data concerning the target and additional segments to a first and/or second image unit 43, 44.

Controller 25 controls X-ray source 30. It may control collimating blades (not shown) inside X-ray 30 for limiting the X-ray irradiation region. Controller 25 also provides a read-out mode control signal and full-well select control signal to X-ray detector 20, more in particular to addressing circuitry 22 and well selector 24, respectively. The read-out mode control signal may also be provided to image constructor 40, more in particular to relay unit 42.

Next, the operation of system 100 will be described based on the mixed read-out mode, the first regular read-out mode, and the second regular read-out mode. During this description it is assumed that controller 25 controls motor 60 to cause a rotational movement of X-ray source 30 and X-ray detector 20 around object 50.

Mixed Read-Out Mode

In the mixed read-out mode, the outputted data stream comprises different sections that relate to different segments. In this mode, well selector 24 may, in response to a full-well select control signal, set the pixels in target segment T to a low full-well capacitance, whereas the pixels in the additional segments A1 . . . A8 may be set to a high full-well capacitance. Additionally, controller 25 may set the collimator blades to a second position in which X-rays are irradiated towards all the segments of X-ray sensor 21.

However, it may also be possible that well selector 24 selects the same full-well capacitance for all the pixels in X-ray sensor 21, for instance the low full-well capacitance. In this case, controller 25 may set the collimator blades to a first position to limit the X-ray irradiation region to target segment T.

Controller 25 provides the read-out mode control signal to addressing circuitry 22 such that addressing circuitry 22 is able to provide the correct addressing of the various segments. This same control signal is provided to relay unit 42.

When relay unit 42 receives part of the data stream stored in buffer 41, it relays the data related to target segment T to first image unit 43. This unit is configured to, when operating the mixed read-out mode, generate a panoramic X-ray image.

Similarly, relay unit 42 relays the data related to the additional segments A1 . . . A8 to second image unit 44. This unit is configured to, when operating the mixed read-out mode, generate a 3D model or one or more second X-ray images. In addition, relay unit 42 may relay data related the target segment T also to second image unit 44 as will be described later.

Assuming that X-ray detector 20 and X-ray source 30 rotate for about 12 seconds around the object to the imaged, and assuming that a first block can be generated in ⅟₃₀ seconds, there is a total of 12*30 first blocks. Assuming that the data stream has the following build up:

||T;A1|T;A2|T;A3|T;A4|T;A5|T;A6|T;A7|T;A8|| it can be concluded that there are 8*12*30 read-outs of the target segment available for first image unit 43. Each of these read-outs corresponds to a different angular position of X-ray detector 20 relative to object 50. This information can be used to generate a panoramic image in a manner known in the art. Furthermore, there are 12*30 read-outs available for each of additional segments A1-A8. This information, in combination with information about target segment T, can be used by second image unit 44 to construct 12*30 second X-ray images, each image comprising information from all the segments. Alternatively, a panoramic image may be formed similar to the panoramic image constructed by first image unit 43, although such image may be prone to blurring. Second image unit 43 may also be configured to generate a 3D model using known CBCT techniques.

In this example, relay unit 42 may be configured to relay all the information about the target segment T to first image unit 43, to relay all the information about additional segments A1 . . . A8 to second image unit 44, and to relay specific information about target segment T to second image constructing unit 44. This latter information is the information that is temporally adjacent to the information that was obtained for the additional segments that are adjacent to the target segment on X-ray sensor 21.

First Regular Read-Out Mode

In the first regular read-out mode, the same full-well capacitance can be selected for all pixels. Moreover, the collimator blades can be set in the second position. Moreover, addressing circuitry 22 now sequentially addresses the segments, preferably in the order the segments are arranged on X-ray sensor 21, e.g. A1, A2, A3, A4, T, A5, A6, A7, A8. In this case, relay unit 42 relays all the information to the second image unit 44, which produces one or more second X-ray images or a 3D model as described above. This mode therefore corresponds to a CBCT mode.

Second Regular Read-Out Mode

In the second regular read-out mode, the same full-well capacitance can be selected for all pixels. Moreover, the collimator blades can be set in the first position. Moreover, addressing circuitry 22 now only addresses target segment T. In this case, relay unit 42 relays all the information to the first image unit 43, which produces a panoramic X-ray images. This mode therefore corresponds to a panoramic mode.

Figure 4:
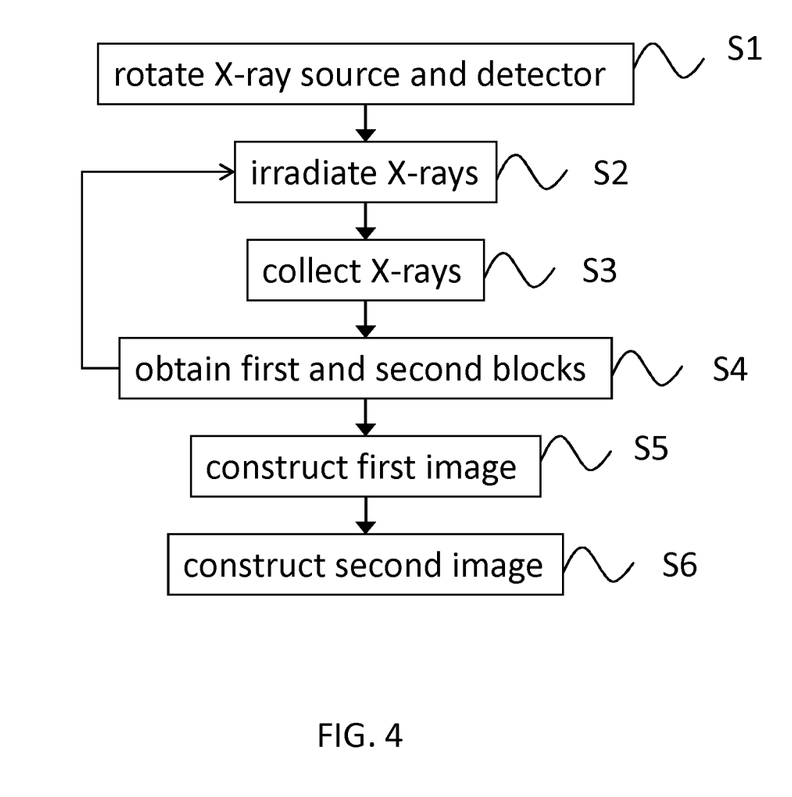
FIG. 4 illustrates a method in accordance with the present invention.

FIG. 4 illustrates an exemplary method in accordance with the present invention. In a first step S1, a rotational movement of an X-ray source and X-ray detector around an object to be imaged is initiated. Next, X-rays are irradiated towards the object, preferably while rotating the X-ray source and detector, in step S2. The X-ray detector collects X-rays that have passed through the object in step S3. More in particular, the X-ray sensor of the X-ray detector comprises a plurality of segments, said plurality of segments comprising a target segment and a plurality of additional segments. In step S4, first and second blocks are obtained. More in particular, first blocks are sequentially obtained from the X-ray sensor, each first block comprising a plurality of sequentially obtained different second blocks, wherein each second block comprises a read-out of the target segment, and wherein more than one of the second blocks comprises a different part of the additional segments such that each first block comprises a read-out for each of the plurality of segments.

Steps S2, S3 and S4 are repeated until the rotation of the X-ray detector and X-ray source has been completed. Then, a first X-ray image is constructed based on the read-outs of the target segment in step S5. In addition, a second X-ray image or 3D model is constructed based on the read-outs of the additional segments and a read-out of the target segment.

The invention claimed is:

1. An X-ray system comprising:
an X-ray source provided with an emitter for emitting X-rays and a collimator for collimating the emitted X-rays;
an X-ray detector system comprising an x-ray detector and an image constructor; and
a mounting frame for moving the X-ray source and X-ray detector around an object to irradiate X-rays from different angles towards the object;
wherein the X-ray detector comprises an X-ray sensor that comprises a plurality of segments, addressing circuitry for individually addressing the segments, and readout circuitry for reading out an addressed segment, said plurality of segments comprising a target segment and a plurality of additional segments;
wherein the X-ray system is configured to obtain a plurality of read-outs of the plurality of segments corresponding to different angles of incidence of the X-rays relative to the object;

wherein the image constructor is configured for constructing a first x-ray image based on the read-outs of the target segment and a 3D model based on the read-outs of the additional segments and a read-out of the target segment;

wherein the X-ray detector is configured to be operable in:
a mixed read-out mode in which an output of the X-ray sensor comprises sequentially obtained first blocks, each first block comprising a plurality of sequentially obtained different second blocks, wherein each second block comprises a read-out of the target segment, and wherein more than one of the second blocks comprises a different part of the additional segments such that each first block comprises a read-out for each of the plurality of segments, and in which mode the image constructor outputs the first X-ray image and the 3D model;
a first regular mode in which the output of the x-ray sensor comprises sequentially obtained third blocks, each third block comprising a single read-out for each of the plurality of segments, and in which mode the image constructor outputs the 3D model;
a second regular mode in which the output of the X-ray sensor comprises sequentially obtained fourth blocks, each fourth block only comprising a single read-out for the target segment and in which mode the image constructor outputs the first X-ray image;
wherein the first X-ray image corresponds to a panoramic image and wherein the 3D model comprises a digital volume of the object, wherein the image constructor is configured to generate the 3D model by cone beam computed tomography (CBCT).

2. The X-ray system according to claim 1, wherein the addressing circuitry is configured to, for said more than one of the second blocks, sequentially address the target segment and said different part of the additional segments, when the X-ray detector operates in the mixed read-out mode.

3. The X-ray system according to claim 1, wherein the number of second blocks equals the number of additional segments.

4. The X-ray system according to claim 1, wherein each of the second blocks comprises a read-out for a different part of the additional segments.

5. The X-ray system according to claim 4, wherein each second block comprises a read-out of the target segment and a single additional segment.

6. The X-ray system according to claim 1, wherein the segments of the X-ray sensor are adjacently arranged in a given direction.

7. The X-ray system according to claim 1, wherein the X-ray sensor comprises a plurality of pixels that are arranged in a plurality of rows and columns, wherein each of the plurality of segments corresponds to a group of rows.

8. The X-ray system according to claim 7, wherein each of the plurality of segments corresponds to an identical number of adjacent rows.

9. The X-ray system according to claim 7, wherein the X-ray sensor comprises a CMOS based X-ray sensor, wherein each pixel comprises a photosensitive element and a storage capacitor, wherein the photosensitive element is configured to change a voltage over the storage capacitor in dependence of an amount incident photons.

10. The X-ray system according to claim 9, wherein the pixels of the X-ray sensor are multi-well pixels that are configured to operate in at least a high full-well mode and in a low full-well mode, wherein a storage capacitance of the pixel in the high full-well mode is larger than that in the low full-well mode, said X-ray detector further comprising a well selector for selecting the low full-well mode or the high full-well mode for all pixels in a given segment.

11. The X-ray system according to claim 10, wherein the well selector is configured to select the high full-well mode for the pixels in the additional segments and to select the low full-well mode for the pixels in the target segment, when the X-ray detector is operating in the mixed read-out mode.

12. The X-ray system according to claim 10, wherein the controller is further configured for providing a full-well select signal to the X-ray sensor to set the full-well capacitance in the pixels of the X-ray sensor.

13. The X-ray system according to claim 9, wherein the well selector is configured to select the same full-well mode for the pixels in the additional segments and the target segment, when the X-ray detector is operating in the first and/or second regular read-out mode.

14. The X-ray system according to claim 9, wherein the well selector is configured to select a low full-well mode for the pixels in the additional segments and a high full-well mode for the pixels in the target segment, when the Xray detector is operating in the second regular read-out mode.

15. The X-ray system according to claim 1, wherein the image constructor comprises:
a first image unit for constructing the first X-ray image;
a second image unit for constructing the 3D model;
a buffer unit for receiving a second block from the read-out circuitry of the X-ray detector;
a relay unit for relaying read-outs pertaining to the target segment in the received second block to the first image unit and for relaying read-outs pertaining to an additional segment in the received second block to the second image unit.

16. The X-ray system according to claim 15, wherein the image constructor is configured to adjust the first X-ray image using the 3D model.

17. The X-ray system according to claim 1, further comprising:
a C-arm to which the X-ray source and X-ray detector are fixedly mounted;
a motor for rotating the C-arm; and
a controller for controlling the motor.

18. The X-ray system according to claim 17, wherein the controller is further configured for controlling the X-ray source and the X-ray detector, said controller being further configured for providing a control signal to the addressing circuitry to set the x-ray detector in a read-out mode among the mixed read-out mode, the first regular read-out mode, and the second regular read-out mode.

19. The X-ray system according to claim 1, wherein the mounting frame is configured to move between angular positions with respect to the object, while the X-rays are being irradiated and while read-outs of the plurality of segments are obtained.

20. The X-ray system according to claim 1, wherein the mounting frame is configured to move between discrete angular positions with respect to the object, at which positions the X-rays are irradiated and the read-outs of the plurality of segments are obtained.

21. A method for constructing an X-ray image, comprising:
irradiating X-rays onto an object to be imaged using an X-ray source;
collecting X-rays from the object to be imaged using an X-ray sensor, wherein the X-ray sensor comprises a plurality of segments that are individually addressable using addressing circuitry, wherein an addressable segment can be read out, and wherein the said plurality of segments comprise a target segment and a plurality of additional segments;

wherein, when operating in a mixed read-out mode, the output of the X-ray sensor comprises sequentially obtained first blocks, each first block comprising a plurality of sequentially obtained different second blocks, wherein each second block comprises a read-out of the target segment, and wherein more than one of the second blocks comprises a different part of the additional segments such that each first block comprises a read-out for each of the plurality of segments;

constructing a first X-ray image based on the read-outs of the target segment;

constructing a 3D model based on the read-outs of the additional segments and a read-out of the target segment; and rotating the X-ray source and X-ray detector around the object to be imaged while sequentially obtaining said first blocks for obtaining a plurality of read-outs of the plurality of segments corresponding to different angles of incidence of the X-rays relative to the object;

wherein the first X-ray image corresponds to a panoramic image and wherein the 3D model comprises a digital volume of the object, wherein the image constructor is configured to generate the 3D model by cone beam computed tomography (CBCT).

22. An X-ray system comprising:

an X-ray source provided with an emitter for emitting X-rays and a collimator for collimating the emitted X-rays;

an X-ray detector system comprising an x-ray detector and an image constructor; and a mounting frame for moving the X-ray source and X-ray detector around an object to irradiate X-rays from different angles towards the object, wherein the X-ray detector comprises an X-ray sensor that comprises a plurality of segments, addressing circuitry for individually addressing the segments, and read-out circuitry for reading out an addressed segment, said plurality of segments comprising a target segment and a plurality of additional segments, wherein the X-ray system is configured to obtain a plurality of read-outs of the plurality of segments corresponding to different angles of incidence of the X-rays relative to the object, wherein the image constructor is configured for constructing a first x-ray image based on the read-outs of the target segment and a 3D model based on the read-outs of the additional segments and a read-out of the target segment, wherein the X-ray detector is configured to be operable in a mixed read-out mode in which an output of the X-ray sensor comprises sequentially obtained first blocks, each first block comprising a plurality of sequentially obtained different second blocks, wherein each second block comprises a read-out of the target segment, and wherein more than one of the second blocks comprises a different part of the additional segments such that each first block comprises a read-out for each of the plurality of segments, and in which mode the image constructor outputs at least one of the first X-ray image and the 3D model, and wherein the first X-ray image corresponds to a panoramic image and wherein the 3D model comprises a digital volume of the object, wherein the image constructor is configured to generate the 3D model by cone beam computed tomography (CBCT).

* * * * *